(12) United States Patent
Stott et al.

(10) Patent No.: US 10,039,724 B2
(45) Date of Patent: Aug. 7, 2018

(54) 7-HYDROXY CANNABIDIOL (7-OH-CBD) FOR USE IN THE TREATMENT OF NON-ALCOHOLIC FATTY LIVER DISEASE (NAFLD)

(71) Applicant: GW Pharma Limited, Histon, Cambridge, Cambridgeshire (GB)

(72) Inventors: Colin Stott, Histon (GB); Marnie Duncan, Histon (GB); Vincenzo Di Marzo, Pozzuoli (IT); Cristoforo Silvestri, Pozzuoli (IT); Andrea Martella, Pozzuoli (IT)

(73) Assignee: GW Research Limited, Cambridge (GB)

( * ) Notice: Subject to any disclaimer, the term of this patent is extended or adjusted under 35 U.S.C. 154(b) by 0 days.

(21) Appl. No.: 15/321,778

(22) PCT Filed: Jun. 29, 2015

(86) PCT No.: PCT/GB2015/051893
§ 371 (c)(1),
(2) Date: Dec. 23, 2016

(87) PCT Pub. No.: WO2015/198077
PCT Pub. Date: Dec. 30, 2015

(65) Prior Publication Data
US 2017/0128385 A1  May 11, 2017

(30) Foreign Application Priority Data

Jun. 27, 2014 (GB) .................................. 1411467.2

(51) Int. Cl.
*A61K 31/05* (2006.01)

(52) U.S. Cl.
CPC .................................. *A61K 31/05* (2013.01)

(58) Field of Classification Search
None
See application file for complete search history.

(56) References Cited

U.S. PATENT DOCUMENTS

2005/0143448 A1  6/2005  Grenard et al.

FOREIGN PATENT DOCUMENTS

| PL | 388833 A1 | 2/2011 |
| WO | WO 2009/093018 A1 | 7/2009 |

OTHER PUBLICATIONS

Osei-Hyiaman et al., J. Clin. Invest. 2005, 115 (5): 1298-305.*
(Continued)

*Primary Examiner* — Karl J Puttlitz
(74) *Attorney, Agent, or Firm* — Wolf, Greenfield & Sacks, P.C.

(57) ABSTRACT

The liver plays a key role in regulating total body energy homeostasis and its ability to do so is greatly affected by the occurrence of pathological conditions such as hepatosteatosis or non-alcoholic fatty liver disease (NAFLD), which contributes to hepatic insulin resistance and potentially end-stage liver disease-related mortality. Triglyceride accumulation in hepatocytes of steatotic livers results from the incorporation of plasma free fatty acids as well as de novo fat synthesis. The present invention relates to the use of 7-hydroxy-cannabidiol (7-OH-CBD) in the treatment of non-alcoholic fatty liver disease (NAFLD). Treatment of NAFLD involves lowering the triglyceride levels in a patient's blood stream.

8 Claims, 2 Drawing Sheets

(56) References Cited

OTHER PUBLICATIONS

Hanus et al., Org. Biomol. Chem., 2005, 3, 1116-1123.*
Supplementary Material for Organic & Biomolecular Chemistry (2005).*
Tam et al., Endocannabinoids in liver disease. Hepatology. Jan. 2011;53(1):346-55. doi: 10.1002/hep.24077.
Wargent et al., The cannabinoid Δ(9)-tetrahydrocannabivarin (THCV) ameliorates insulin sensitivity in two mouse models of obesity. Nutr Diabetes. May 27, 2013;3:e68. doi:10.1038/nutd.2013.9.
Yang et al., Cannabidiol protects liver from binge alcohol-induced steatosis by mechanisms including inhibition of oxidative stress and increase in autophagy. Free Radic Biol Med. Mar. 2014;68:260-7. doi: 10.1016/j.freeradbiomed.2013.12.026. Epub Jan. 4, 2014.

\* cited by examiner

Figure 1. Adipored staining of triglycerides in HHL5 cells
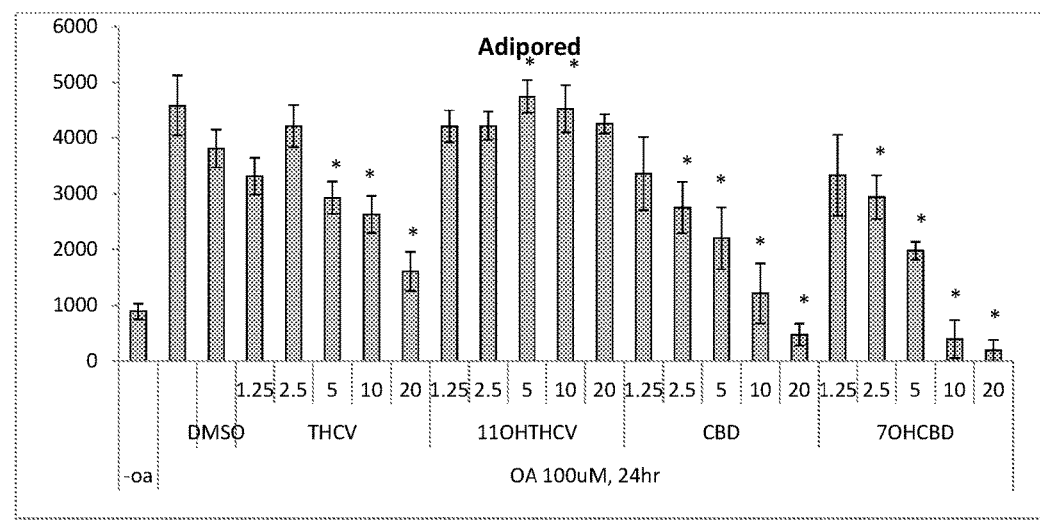
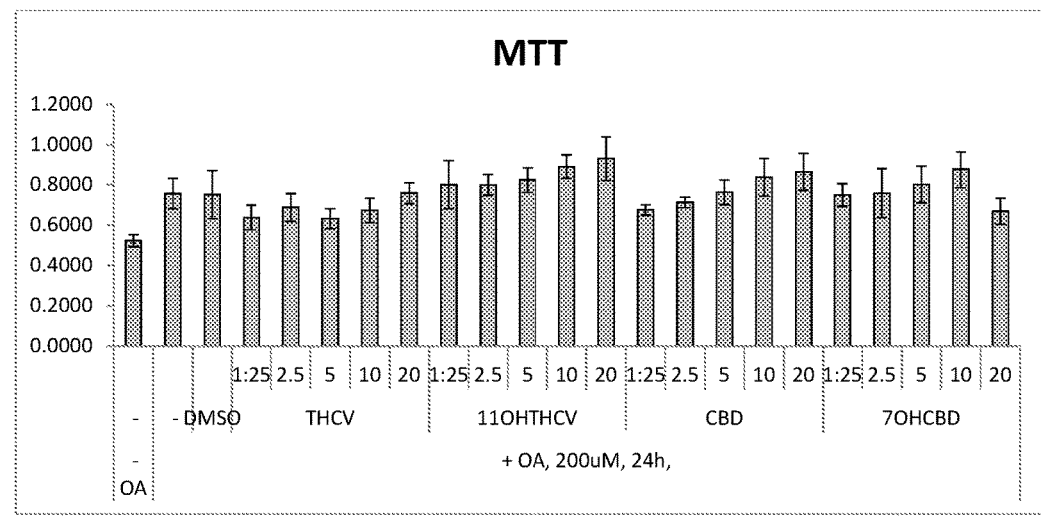

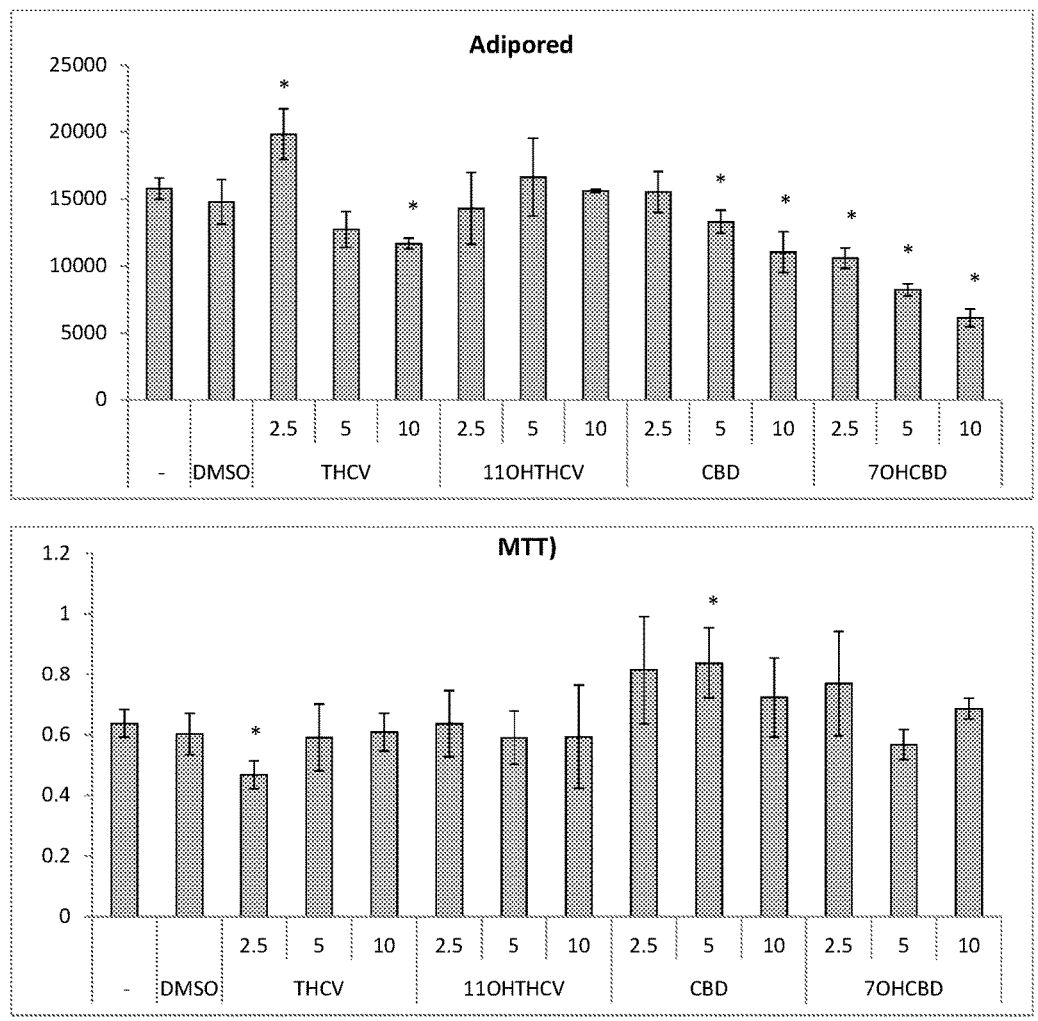
Figure 2. Adipored staining of triglycerides in 3T3-L1-derived mature adipocytes

7-HYDROXY CANNABIDIOL (7-OH-CBD) FOR USE IN THE TREATMENT OF NON-ALCOHOLIC FATTY LIVER DISEASE (NAFLD)

RELATED APPLICATION

This application is a national stage filing under 35 U.S.C. § 371 of International Application No. PCT/GB2015/051893, filed Jun. 29, 2015, which was published under PCT Article 21(2) in English, the entire disclosure of which is incorporated by reference herein in its entirety.

The present invention relates to the use of 7-hydroxy-cannabidiol (7-OH-CBD) in the treatment of non-alcoholic fatty liver disease (NAFLD). Treatment of NAFLD involves lowering the triglyceride levels in a patient's blood stream.

BACKGROUND TO THE INVENTION

The liver plays a key role in regulating total body energy homeostasis and its ability to do so is greatly affected by the occurrence of pathological conditions such as hepatosteatosis or non-alcoholic fatty liver disease (NAFLD), which contributes to hepatic insulin resistance and potentially end-stage liver disease-related mortality. Triglyceride accumulation in hepatocytes of steatotic livers results from the incorporation of plasma free fatty acids as well as de novo fat synthesis.

Non-alcoholic fatty liver disease (NAFLD) is the term for a wide range of conditions caused by a build-up of fat within the liver cells. It is usually seen in people who are overweight or obese. If the build-up of fat increases, inflammation and scarring of the liver may occur.

People who are obese and have NAFLD are more at risk of suffering from a heart attack or a stroke. Indeed NAFLD is associated with; obesity; type II diabetes; high blood pressure; and high cholesterol.

Treatment of NAFLD involves weight loss and exercise; reducing the levels of triglycerides in the blood and reducing the level of glucose in the blood.

There are currently no specific medicines for NAFLD, but certain medicines used to treat high blood pressure and diabetes also have a beneficial effect on the liver. NAFLD may go on to cause cirrhosis or liver cancer and as such early and effective treatment is essential.

The primary goal for the clinical management of NAFLD is to reduce the risk of cardiovascular disease and type II diabetes. The risks of these diseases are highly diminished by reducing triglyceride levels in the blood including LDL cholesterol, reducing blood pressure, and reducing blood glucose levels.

Triglycerides (TG) are fat molecules which circulate in the blood, and are used to provide energy to the body, but excess TG which are not used are stored. High triglyceride levels are linked to a greater chance of heart disease and other metabolic disorders.

Triglycerides are the end product of digesting and breaking down fats in meals. Some triglycerides are made in the body from other energy sources such as carbohydrates. A healthy diet and exercise plan can lower triglyceride levels, improve cholesterol, and lower the risk of heart disease although this is sometimes difficult to achieve.

High triglyceride levels can also be caused by mediations such as beta blockers; ACE inhibitors; diuretics; hormonal contraceptives; immunosuppressants; HIV treatments; and anti-psychotics.

Lowering TG levels in the blood can help reduce the risk of suffering from heart disease, diabetes and other metabolic disorders.

It has been shown previously that tetrahydrocannabivarin (THCV) is able to decrease triglyceride levels in HHL-5 cells treated with oleic acid. This is an in vitro model for fatty liver disease which showed that THCV was able to reduce triglyceride (TG) levels in a time dependent manner (Wargent et al., 2013).

It has also been suggested that cannabidiol (CBD) may be useful in reducing TG levels in blood (WO 2009/093018).

Yang et al. (2014) describes that CBD may protect the liver from the effects of binge alcohol-induced steatosis.

The Polish patent application PL 388833 describes the use of CBD for reducing body weight gain and reducing excessive fat accumulation.

Surprisingly, it has now been found that a metabolite of CBD, 7-hydroxy-cannabidiol, (7-OH CBD) is able to decrease intracellular TG levels in an in vitro model of fatty liver disease; furthermore it was more potent than its parent compound CBD. Conversely a metabolite of THCV, 11-hydroxy-tetrahydrocannabivarin, (11-OH-THCV) had no effect on the TG levels which infers that not all metabolites are effective in the same way as their parent compounds.

DEFINITIONS AND ABBREVIATIONS

Definitions of some of the terms used to describe the invention are detailed below:

The phytocannabinoids described in the present application are listed below along with their standard abbreviations.

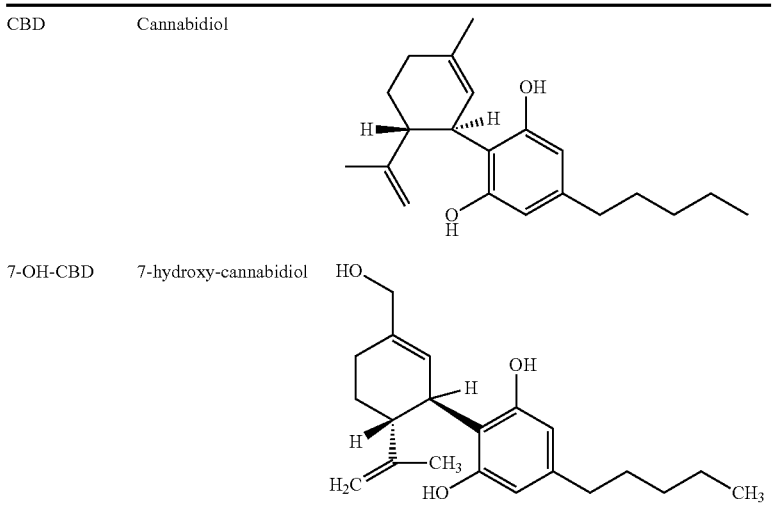

CBD     Cannabidiol

7-OH-CBD     7-hydroxy-cannabidiol

-continued

| | | |
|---|---|---|
| THCV | Tetrahydrocannabivarin | |
| 11-OH-THCV | 11-hydroxy-tetrahydrocannabivarin | |

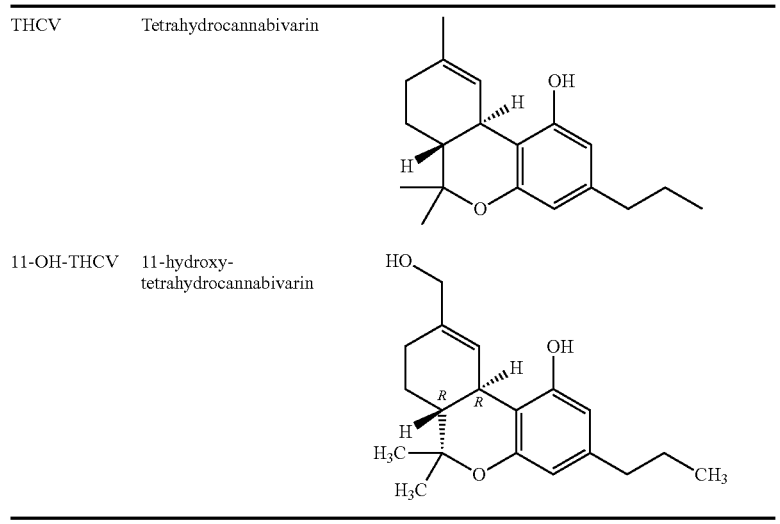

The table above is not exhaustive and merely details the cannabinoids which are identified in the present application for reference. So far over 60 different cannabinoids have been identified and these cannabinoids can be split into different groups as follows: Phytocannabinoids; Endocannabinoids and Synthetic cannabinoids (which may be novel cannabinoids or synthetically produced phytocannabinoids or endocannabinoids).

"Phytocannabinoids" are cannabinoids that originate from nature and can be found in the cannabis plant. The phytocannabinoids can be isolated from plants to produce a highly purified extract or can be reproduced synthetically.

"Highly purified cannabinoid extracts" are defined as cannabinoids that have been extracted from the cannabis plant and purified to the extent that other cannabinoids and non-cannabinoid components that are co-extracted with the cannabinoids have been substantially removed, such that the highly purified cannabinoid is greater than or equal to 98% (w/w) pure.

"Synthetic cannabinoids" are compounds that have a cannabinoid or cannabinoid-like structure and are manufactured using chemical means rather than by the plant.

Phytocannabinoids can be obtained as either the neutral (decarboxylated form) or the carboxylic acid form depending on the method used to extract the cannabinoids. For example it is known that heating the carboxylic acid form will cause most of the carboxylic acid form to decarboxylate into the neutral form.

BRIEF SUMMARY OF THE DISCLOSURE

In accordance with a first aspect of the present invention there is provided a pharmaceutical composition comprising 7-hydroxy-cannabidiol (7-OH-CBD) and a pharmaceutically acceptable carrier for use in the treatment of non-alcoholic fatty liver disease (NAFLD).

In one embodiment the treatment involves lowering triglyceride levels. The high triglyceride levels may be caused by obesity; type II diabetes; or medication.

Preferably the dose of 7-OH-CBD is between 1 and 1000 mg/kg day.

The pharmaceutical composition may comprise 7-OH-CBD in combination with another medicament. Preferably the 7-OH-CBD may be formulated for administration separately, sequentially or simultaneously with the other medicament or the combination may be provided in a single dosage form.

Preferably the 7-OH-CBD is in a pure, isolated or synthetic form.

It is envisaged that the composition be administered as an oral liquid solution. Other modes of administration including solids, semi-solids, gels, sprays, aerosols, inhalers, vaporisers, enemas and suppositories are alternative administration forms. Such medicaments could be administered via the oral, buccal, sublingual, respiratory, nasal and distal rectum route.

In accordance with a second aspect of the present invention there is provided a method of treating non-alcoholic fatty liver disease (NAFLD) comprising administering a therapeutically effective amount of 7-hydroxy-cannabidiol (7-OH-CBD) to a subject in need thereof.

BRIEF DESCRIPTION OF THE DRAWINGS

Embodiments of the invention are further described hereinafter with reference to the accompanying drawings, in which:

FIG. 1 shows Adipored staining of triglycerides in HHL5 cells; and

FIG. 2 shows Adipored staining of triglycerides in 3T3-L1-derived mature adipocytes.

Legend To The Figures

FIG. 1. THCV, CBD and 7-OH-CBD decrease Adipored staining of triglycerides in HHL5 cells in a dose dependent manner. HHL5 cells in 96-well plates at 90% confluence treated without or with 100 uM oleic acid in the absence or presence of THCV, 11-OH-THCV, CBD or 7-OH-CBD at the indicated concentrations (uM) assayed for intracellular triglyceride levels using AdipoRed (Lonza) (top) or cell viability via MTT (bottom). Data is expressed as the average and standard deviation of signals from 4 wells. *P<0.05.

FIG. 2. THCV, CBD and 7-OH-CBD decrease Adipored staining of triglycerides in 3T3-L1-derived mature adipocytes in a dose dependent manner. 3T3-L1 cells were grown and differentiated in 100 mm plates for 5 days before being transferred to 96-well plates, at d7 the cells were treated with THCV, 11-OH-THCV, CBD or 7-OH-CBD at the indicated concentrations (uM) for 48 hours prior to analysis of assayed intracellular triglyceride levels using AdipoRed (Lonza) (top) or cell viability via MTT (bottom). Data is expressed as the average and standard deviation of signals from 4 wells. *P<0.05.

DETAILED DESCRIPTION

The Example below describes the use of an in vitro model of fatty liver disease to demonstrate the efficacy of CBD, THCV and their primary metabolites 7-OH-CBD and 11-OH-THCV respectively in reducing triglyceride levels.

7-OH-CBD is the primary metabolite of its parent compound CBD and 11-OH-THCV is the primary metabolite of its parent compound THCV.

EXAMPLE 1

Materials and Methods
  Cell Culture:
  HHL-5 cells were cultured in standard growth media (DMEM [Lonza] supplemented with 10% FBS [Lonza], NEAA [Gibco] and Pen.Strep [Gibco]). 3T3-L1 cells were cultured in growth media (GM; DMEM [Lonza] low NaHCO3 (1.5 g/l), supplemented with 10% FBS [Lonza] and pen./strep. [Gibco]).
  In order to induce adipogenesis cells were grown to 100% confluence and then switched to differentiation media (DMEM [Lonza] supplemented with a specific lot of 10% FBS [Lonza], 1 ug/ml Insulin (Sigma), 250 nM Dexamethasone (Sigma), 500 uM MIX (Sigma) and pen./strep. [Gibco]) for 2 days, followed by incubation in DMEM [Lonza] supplemented with a specific lot of 10% FBS [Lonza], 1 ug/ml Insulin (Sigma) and pen./strep. [Gibco] until day 7-10 at which point mature adipocytes are treated with cannabinoids at the indicated concentrations.
  Triglyceride Level Analysis in Cells:
  HHL5 cells seeded in 96-well plates were grown to 90% confluence and then treated with 100 uM oleic acid (OA) or DMSO (−) for 24 hours in the absence or presence of cannabinoids at the indicated concentrations.
  3T3-L1 cells were plated in 100 mm plates and differentiated as above to obtain mature adipocytes, at which point they were re-plated into 96-well plates and then treated with the indicated concentrations of cannabinoids for 2 days. Cells were then washed with PBS and stained with AdipoRed (Lonza) and read with a Genios Pro Plate reader (Tecan) according to the manufacturer's instructions.
  MTT Assay:
  MTT (3-[4,5-dimethyltiazol-2yl]-2,5 diphenyltetrazolium bromide) (5 mg/ml differentiation media) was added to cells treated as described above, and cells were incubated for additional 1 h at 37 C.
  Cells were then washed in PBS and dried before the addition of 100 ul of isopropanol to dissolve the formazan precipitate. The OD of each well was measured with a Genios-Pro plate reader (Tecan) equipped with a 620-nm filter.
Results
  HHL5 hepatocytes that have been treated with oleic acid to induce intracellular lipid accumulation are a useful in vitro model for fatty liver disease.
  THCV and CBD, when metabolized by the liver result in the formation of the metabolites 11-OH-THCV and 7-OH-CBD (among others) respectively.
  The ability of purified 11-OH-THCV and 7-OH-CBD, to modulate intracellular lipid levels in the in vitro hepatosteatosis model system was tested to determine if the metabolism of THCV and CBD resulted in compounds (metabolites) that were more, or less, active than their parent cannabinoids.
  Upon co-incubation of HHL5 cells with 100 uM oleic acid with the above mentioned compounds for 24 hr we found that, THCV and CBD both dose-dependently lowered intracellular lipid levels.
  FIG. 1 shows that the metabolite of THCV, 11-OH-THCV, was devoid of lipid lowering activity, and the metabolite of CBD, 7-OH-CBD, was effective at lowering TG levels. Indeed the 7-OH-CBD compound was even more potent that its parent compound CBD (FIG. 1, top).
  HHL5 cells treated in parallel were also assessed for viability using the MTT assay, and no toxicity was found for THCV or CBD up to 20 uM. Similarly, neither 11-OH-THCV or 7-OH-CBD were found to be toxic, indicating that the observed decreases in lipid content were not due to toxicity (FIG. 1, bottom).
  Adipocytes are the major biological store of triglycerides. The in vitro production of mature 3T3-L1-derived adipocytes, allows the effects of cannabinoids on the lipid content of a relatively pure pool of adipocytes to be examined.
  As shown in FIG. 2 (top), just as in HHL5 hepatocytes, THCV, CBD and 7-OH-CBD all dose-dependently decreased intracellular lipid stores within mature 3T3-L1-derived adipocytes, while again, 11-OH-THCV had no effect.

DISCUSSION

The data presented in this Example reinforce the previously reported studies that THCV and CBD may be useful agents for regulating lipid metabolism.

Interestingly, the metabolites of these cannabinoids, 11-OH-THCV and 7-OH-CBD differ in their abilities to modulate lipid levels.

While 11-OH-THCV appears to be inactive, 7-OH-CBD appears to be more active than CBD.

These data confirm that like in hepatocytes, THCV and CBD are able to reduce lipid levels within in vitro derived mature 3T3-L1 adipocytes. Further, as in hepatocytes, while 11-OH-THCV had no effect on lipid levels, 7-OH-CBD was more efficacious than CBD at reducing Adipored staining in mature adipocytes. These results were not associated with any apparent effect on cellular viability based on the MTT assay.

The surprising ability of the 7-OH-CBD metabolite to reduce triglyceride levels therefore makes this a potentially useful treatment of metabolic disorders by lowering triglyceride (cholesterol) levels in the blood stream. The fact that 7-OH-CBD appears more potent than its parent cannabinoid, CBD, means that lower doses of 7-OH-CBD may be used in the treatment of NAFLD.

REFERENCES

Wargent et al., (2013) The cannabinoid Δ(9)-tetrahydrocannabivarin (THCV) ameliorates insulin sensitivity in two mouse models of obesity. Nutr. Diabetes. 27:3e68.
Yang et al. (2014) Free Radical Biology and Medicine, vol. 68, 2014, 260-267 "Cannabidiol protects liver from binge alcohol-induced steatosis by mechanisms including inhibition of oxidative stress and increase in autophagy."

The invention claimed is:
1. A method of treating non-alcoholic fatty liver disease (NAFLD), the method comprising administering to a subject in need thereof a therapeutically effective amount of a pharmaceutical composition comprising 7-hydroxy-cannabidiol (7-OH-CBD):

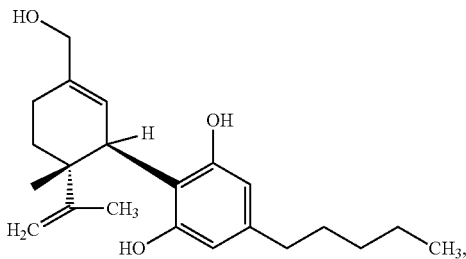 [SMILES: C=C(C)[C@]1(C)CCC(CO)=C[C@H]1c1c(O)cc(CCCCC)cc1O]

and a pharmaceutically acceptable carrier.

2. The method as claimed in claim 1, wherein the treatment involves lowering triglyceride levels.

3. The method as claimed in claim 2, wherein the high triglyceride levels are caused by obesity.

4. The method as claimed in claim 2, wherein the high triglyceride levels are caused by type II diabetes.

5. The method as claimed in claim 2, wherein the high triglyceride levels are caused by medication.

6. The method as claimed in claim 1, wherein the dose of 7-OH-CBD is between 1 and 1000 mg/kg day.

7. The method as claimed in claim 1, wherein the 7-OH-CBD is used in combination with another medicament, wherein the 7-OH-CBD may be formulated for administration separately, sequentially or simultaneously with the other medicament or the combination may be provided in a single dosage form.

8. The method as claimed in claim 1, wherein the 7-OH-CBD is in a pure, isolated or synthetic form.

* * * * *